(12) United States Patent
Libbus et al.

(10) Patent No.: US 8,452,398 B2
(45) Date of Patent: May 28, 2013

(54) METHOD AND APPARATUS FOR SYNCHRONIZING NEURAL STIMULATION TO CARDIAC CYCLES

(75) Inventors: Imad Libbus, St. Paul, MN (US); Paul A. Haefner, Circle Pines, MN (US); Aaron R. McCabe, Minneapolis, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1010 days.

(21) Appl. No.: 12/469,012

(22) Filed: May 20, 2009

(65) Prior Publication Data

US 2009/0228060 A1 Sep. 10, 2009

Related U.S. Application Data

(62) Division of application No. 11/099,141, filed on Apr. 5, 2005, now Pat. No. 7,542,800.

(51) Int. Cl.
*A61N 1/365* (2006.01)
(52) U.S. Cl.
USPC .................................................. 607/9; 607/7
(58) Field of Classification Search
USPC ........................................................ 607/7, 9
See application file for complete search history.

(56) References Cited

U.S. PATENT DOCUMENTS

| | | | |
|---|---|---|---|
| 3,421,511 A | 1/1969 | Schwartz et al. |
| 3,650,277 A | 3/1972 | Sjostrand et al. |
| 4,541,432 A | 9/1985 | Molina-Negro et al. |
| 4,759,368 A | 7/1988 | Spanton et al. |
| 4,763,646 A | 8/1988 | Lekholm |
| 4,791,931 A | 12/1988 | Slate |
| 4,938,223 A | 7/1990 | Charters et al. |
| 5,111,815 A | 5/1992 | Mower |
| 5,190,035 A | 3/1993 | Salo et al. |
| 5,199,428 A | 4/1993 | Obel et al. |
| 5,203,326 A | 4/1993 | Collins |
| 5,243,980 A | 9/1993 | Mehra |
| 5,318,592 A | 6/1994 | Schaldach |

(Continued)

FOREIGN PATENT DOCUMENTS

| | | |
|---|---|---|
| EP | 1426078 A1 | 6/2004 |
| EP | 1421973 A3 | 7/2004 |

(Continued)

OTHER PUBLICATIONS

"Japanese Application Serial No. 2008-505371, Office Action mailed Oct. 21, 2011", (w/ English Translation), 14 pgs.

(Continued)

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

A neural stimulator senses a reference signal indicative of cardiac cycles each including a predetermined type timing reference event using a sensor external to the heart and blood vessels. The delivery of the neural stimulation pulses are synchronized to that timing reference event. Examples of the timing reference event include a predetermined cardiac event such as a P-wave or an R-wave detected from a subcutaneous ECG signal, a predetermined type heart sound detected from an acoustic signal, and a peak detected from a hemodynamic signal related to blood flow or pressure.

20 Claims, 5 Drawing Sheets

U.S. PATENT DOCUMENTS

| | | | |
|---|---|---|---|
| 5,330,507 A | 7/1994 | Schwartz | |
| 5,356,425 A | 10/1994 | Bardy et al. | |
| 5,403,351 A | 4/1995 | Saksena | |
| 5,411,531 A | 5/1995 | Hill et al. | |
| 5,437,285 A | 8/1995 | Verrier et al. | |
| 5,507,784 A | 4/1996 | Hill et al. | |
| 5,522,854 A | 6/1996 | Ideker et al. | |
| 5,578,061 A | 11/1996 | Stroetmann et al. | |
| 5,658,318 A | 8/1997 | Stroetmann et al. | |
| 5,690,681 A | 11/1997 | Geddes et al. | |
| 5,700,282 A | 12/1997 | Zabara | |
| 5,731,848 A | 3/1998 | Patel et al. | |
| 5,916,239 A | 6/1999 | Geddes et al. | |
| 5,928,272 A | 7/1999 | Adkins et al. | |
| 6,006,134 A | 12/1999 | Hill et al. | |
| 6,058,331 A | 5/2000 | King | |
| 6,073,048 A | 6/2000 | Kieval et al. | |
| 6,134,470 A | 10/2000 | Hartlaub | |
| 6,161,042 A | 12/2000 | Hartley et al. | |
| 6,178,349 B1 | 1/2001 | Kieval | |
| 6,181,966 B1 | 1/2001 | Nigam | |
| 6,240,314 B1 | 5/2001 | Plicchi et al. | |
| 6,272,377 B1 | 8/2001 | Sweeney et al. | |
| 6,285,909 B1 | 9/2001 | Sweeney et al. | |
| 6,292,695 B1 | 9/2001 | Webster, Jr. et al. | |
| 6,371,922 B1 | 4/2002 | Baumann et al. | |
| 6,400,982 B2 | 6/2002 | Sweeney et al. | |
| 6,415,183 B1 | 7/2002 | Scheiner et al. | |
| 6,421,557 B1 | 7/2002 | Meyer | |
| 6,449,507 B1 | 9/2002 | Hill et al. | |
| 6,473,644 B1 | 10/2002 | Terry, Jr. et al. | |
| 6,487,450 B1 | 11/2002 | Chen | |
| 6,493,585 B2 | 12/2002 | Plicchi et al. | |
| 6,511,500 B1 | 1/2003 | Rahme | |
| 6,522,926 B1 | 2/2003 | Kieval et al. | |
| 6,532,388 B1 | 3/2003 | Hill et al. | |
| 6,542,774 B2 | 4/2003 | Hill et al. | |
| 6,564,096 B2 | 5/2003 | Mest | |
| 6,611,713 B2 | 8/2003 | Schauerte | |
| 6,622,041 B2 | 9/2003 | Terry, Jr. et al. | |
| 6,628,987 B1 | 9/2003 | Hill et al. | |
| 6,631,290 B1 | 10/2003 | Guck et al. | |
| 6,850,801 B2 | 2/2005 | Kieval et al. | |
| 6,985,774 B2 | 1/2006 | Kieval et al. | |
| 7,123,961 B1 | 10/2006 | Kroll et al. | |
| 7,123,967 B2 | 10/2006 | Weinberg | |
| 7,158,832 B2 | 1/2007 | Kieval et al. | |
| 7,299,086 B2 | 11/2007 | McCabe et al. | |
| 7,542,800 B2 | 6/2009 | Libbus et al. | |
| 7,570,999 B2 | 8/2009 | Libbus et al. | |
| 7,587,238 B2 | 9/2009 | Moffitt et al. | |
| 7,623,926 B2 | 11/2009 | Rossing et al. | |
| 7,657,312 B2 | 2/2010 | Pastore et al. | |
| 7,660,628 B2 | 2/2010 | Libbus et al. | |
| 7,769,450 B2 | 8/2010 | Libbus et al. | |
| 7,783,353 B2 | 8/2010 | Libbus et al. | |
| 7,801,601 B2 | 9/2010 | Maschino et al. | |
| 7,831,305 B2 | 11/2010 | Gliner | |
| 7,840,271 B2 | 11/2010 | Kieval et al. | |
| 7,873,413 B2 | 1/2011 | McCabe et al. | |
| 8,000,793 B2 | 8/2011 | Libbus | |
| 8,126,560 B2 | 2/2012 | Scheiner et al. | |
| 8,175,705 B2 | 5/2012 | Libbus | |
| 8,285,389 B2 | 10/2012 | Libbus et al. | |
| 2002/0026221 A1 | 2/2002 | Hill et al. | |
| 2002/0026222 A1 | 2/2002 | Schauerte et al. | |
| 2002/0058877 A1 | 5/2002 | Baumann et al. | |
| 2002/0068875 A1 | 6/2002 | Schroeppel et al. | |
| 2002/0107553 A1 | 8/2002 | Hill et al. | |
| 2002/0120304 A1 | 8/2002 | Mest | |
| 2002/0123769 A1 | 9/2002 | Panken et al. | |
| 2002/0143369 A1 | 10/2002 | Hill et al. | |
| 2002/0165586 A1 | 11/2002 | Hill et al. | |
| 2003/0003052 A1 | 1/2003 | Hampton | |
| 2003/0004549 A1 | 1/2003 | Hill et al. | |
| 2003/0040774 A1* | 2/2003 | Terry et al. ........................ 607/2 |
| 2003/0045909 A1 | 3/2003 | Gross et al. | |
| 2003/0060848 A1 | 3/2003 | Keival et al. | |
| 2003/0060857 A1 | 3/2003 | Perrson et al. | |
| 2003/0060858 A1 | 3/2003 | Kieval et al. | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0149450 A1 | 8/2003 | Mayberg | |
| 2003/0195571 A1 | 10/2003 | Burnes et al. | |
| 2003/0199936 A1 | 10/2003 | Struble et al. | |
| 2003/0212440 A1 | 11/2003 | Boveja | |
| 2003/0229380 A1 | 12/2003 | Adams et al. | |
| 2004/0049120 A1 | 3/2004 | Cao et al. | |
| 2004/0068299 A1 | 4/2004 | Laske et al. | |
| 2004/0088009 A1 | 5/2004 | Degroot | |
| 2004/0127792 A1 | 7/2004 | Siejko et al. | |
| 2004/0138719 A1 | 7/2004 | Cho et al. | |
| 2004/0193231 A1 | 9/2004 | David et al. | |
| 2004/0254616 A1 | 12/2004 | Rossing et al. | |
| 2005/0027320 A1 | 2/2005 | Nehls et al. | |
| 2005/0055060 A1 | 3/2005 | Koh et al. | |
| 2005/0096705 A1 | 5/2005 | Pastore et al. | |
| 2005/0143779 A1 | 6/2005 | Libbus | |
| 2005/0143785 A1 | 6/2005 | Libbus | |
| 2005/0148896 A1 | 7/2005 | Siejko et al. | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0197674 A1 | 9/2005 | McCabe et al. | |
| 2005/0261741 A1 | 11/2005 | Libbus et al. | |
| 2006/0004417 A1 | 1/2006 | Rossing et al. | |
| 2006/0079945 A1 | 4/2006 | Libbus | |
| 2006/0106429 A1 | 5/2006 | Libbus et al. | |
| 2006/0116737 A1 | 6/2006 | Libbus | |
| 2006/0122675 A1 | 6/2006 | Libbus et al. | |
| 2006/0206154 A1 | 9/2006 | Moffitt et al. | |
| 2006/0217772 A1 | 9/2006 | Libbus et al. | |
| 2006/0224188 A1 | 10/2006 | Libbus et al. | |
| 2006/0241725 A1 | 10/2006 | Libbus et al. | |
| 2006/0271108 A1 | 11/2006 | Libbus et al. | |
| 2007/0021799 A1 | 1/2007 | Kieval et al. | |
| 2007/0142864 A1 | 6/2007 | Libbus et al. | |
| 2008/0167693 A1 | 7/2008 | Kieval et al. | |
| 2009/0018596 A1 | 1/2009 | Kieval | |
| 2010/0023090 A1 | 1/2010 | Jaax et al. | |
| 2010/0121399 A1 | 5/2010 | Mccabe et al. | |
| 2010/0286740 A1 | 11/2010 | Libbus et al. | |
| 2011/0082514 A1 | 4/2011 | Libbus et al. | |
| 2011/0106199 A1 | 5/2011 | Mccabe et al. | |
| 2011/0295333 A1 | 12/2011 | Libbus | |
| 2012/0215279 A1 | 8/2012 | Libbus | |

FOREIGN PATENT DOCUMENTS

| | | |
|---|---|---|
| JP | 61-61241 U | 4/1987 |
| JP | 6-246010 A | 9/1994 |
| JP | 11500930 A | 1/1999 |
| JP | 2001-198228 A | 7/2001 |
| JP | 2002-514478 A | 5/2002 |
| JP | 2002513656 A | 5/2002 |
| JP | 2004-523266 A | 8/2004 |
| JP | 2004523265 A | 8/2004 |
| JP | 2004-526471 A | 9/2004 |
| JP | 2005501617 A | 1/2005 |
| WO | WO-9625978 A1 | 8/1996 |
| WO | WO-99/58191 A1 | 11/1999 |
| WO | WO-9956822 A1 | 11/1999 |
| WO | WO-02/26314 A1 | 4/2002 |
| WO | WO-0247761 A2 | 6/2002 |
| WO | WO-03/018108 A3 | 3/2003 |
| WO | WO-03020364 A2 | 3/2003 |
| WO | WO-03/076008 A1 | 9/2003 |
| WO | WO-03/099377 A1 | 12/2003 |
| WO | WO-2005000396 A1 | 1/2005 |

| | | | |
|---|---|---|---|
| WO | WO-2006031331 | A1 | 3/2006 |
| WO | WO-2006/044025 | A1 | 4/2006 |
| WO | WO-2006/107675 | A1 | 10/2006 |
| WO | WO-2008/063396 | A1 | 5/2008 |
| WO | WO-2008/144354 | A1 | 11/2008 |
| WO | WO-2011/088222 | A1 | 7/2011 |

OTHER PUBLICATIONS

Libbus, I., "Implantable Systems and Devices for Providing Cardiac Defibrillation and Apnea Therapy", U.S. Appl. No. 13/198,477, filed Aug. 4, 2011, 70 pgs.

"U.S. Appl. No. 11/459,481, Notice of Allowance mailed Sep. 20, 2010", 7 pgs.

"U.S. Appl. No. 11/459,481, Restriction Requirement mailed Jan. 29, 2010", 6 pgs.

"U.S. Appl. No. 11/459,481, Final Office Action mailed May 17, 2010", 11 pgs.

"U.S. Appl. No. 11/459,481, Response filed Jan. 29, 2009 to Restriction Requirement mailed Dec. 30, 2008", 10 pgs.

"U.S. Appl. No. 11/459,481, Response filed Aug. 17, 2010 to Final Office Action mailed May 17, 2010", 9 pgs.

"U.S. Appl. No. 11/459,481, Response filed Nov. 25, 2009 to Non Final Office Action mailed May 28, 2009", 14 pgs.

"U.S. Appl. No. 11/459,481, Response filed Feb. 10, 2010 to Restriction Requirement mailed Jan. 29, 2010", 8 pgs.

"U.S. Appl. No. 12/126,182, Non-Final Office Action mailed Jul. 23, 2010", 9 pgs.

"U.S. Appl. No. 12/126,182, Response flied Oct. 25, 2010 to Non Final Office Action mailed Jul. 23, 2010", 12 pgs.

"European Application Serial No. 06739916.2, Office Action mailed Jun. 22, 2010", 2 pgs.

"European Application Serial No. 06739916.2, Response filed Dec. 9, 2010 to Office Action dated Jun. 22, 2010", 11 pgs.

Libbus, I., et al., "Hypertension Therapy Based on Activity and Circadian Rhythm", U.S. Appl. No. 12/968,797, filed Dec. 15, 2010, 75 pgs.

"Japanese Application Serial No. 2008-505371, Response filed Jan. 31, 2012 to Office Action mailed Oct. 21, 2011", 12 pgs.

"U.S. Appl. No. 12/126,182, Notice of Allowance mailed Apr. 18, 2011", 12 pgs.

"U.S. Appl. No. 10/746,846, Final Office Action mailed Jan. 23, 2008", 18 pgs.

"U.S. Appl. No. 10/746,846, Final Office Action mailed Feb. 12, 2007", 17 pgs.

"U.S. Appl. No. 10/746,846, Non Final Office Action mailed Apr. 26, 2007", 18 pgs.

"U.S. Appl. No. 10/746,846, Non Final Office Action mailed Jul. 25, 2006", 15 pgs.

"U.S. Appl. No. 10/746,846, Response filed Apr. 17, 2007 to Final Office Action mailed Feb. 12, 2007", 16 pgs.

"U.S. Appl. No. 10/746,846, Response filed Oct. 26, 2007 to Non Final Office Action mailed Apr. 26, 2007", 11 pgs.

"U.S. Appl. No. 10/746,846, Response filed Nov. 9, 2006 to Non Final Office Action mailed Jul. 25, 2006", 17 pgs.

"U.S. Appl. No. 10/746,846, Restriction Requirement mailed Jun. 9, 2006", 7 pgs.

"U.S. Appl. No. 10/746,846, Response filed Jul. 7, 2006 to Restriction Requirement mailed Jun. 9, 2006", 13 pgs.

"U.S. Appl. No. 11/099,141, Final Office Action mailed Oct. 22, 2007", 9 pgs.

"U.S. Appl. No. 11/099,141, Non-Final Office Action mailed May 6, 2008", 11 pgs.

"U.S. Appl. No. 11/099,141, Response filed Jan. 6, 2009 to Final Final Office Action mailed Nov. 7, 2008", 9 pgs.

"U.S. Appl. No. 11/099,141,Response filed Feb. 19, 2008 to Final Office Action mailed Oct. 22, 2007", 13 pgs.

"U.S. Appl. No. 11/099,141, Response filed Apr. 5, 2007 to Restriction Requirement mailed Mar. 6, 2007", 11 pgs.

"U.S. Appl. No. 11/099,141, Response filed Aug. 4, 2008 to Non Final Office Action mailed May 6, 2008", 10 pgs.

"U.S. Appl. No. 11/099,141, Restriction Requirement mailed Mar. 6, 2007", 6 pgs.

"U.S. Appl. No. 11/099,141, Final Office Action mailed Nov. 7, 2008", 8 pgs.

"U.S. Appl. No. 11/099,141, Response filed Aug. 20, 2007 to Non Final Office Action mailed May 18, 2007", 11 pgs.

"U.S. Appl. No. 11/099,141, Notice of Allowance mailed Jan. 28, 2009", 4 pgs.

"U.S. Appl. No. 11/099,141, Non-Final Office Action mailed May 18, 2007", 8 pgs.

"International Search Report and Written Opinion for Application No. PCT/US2006/011446, dated Aug. 25, 2006", 16 pgs.

Andersen, H., "Long-term follow-up of patients from a randomised trial of atrial versus ventricular pacing for sick-sinus syndrome", *Lancet*, 350(9086), (Oct. 25, 1997), 1210-6.

Benchimol, A, "Cardiac hemodynamics during stimulation of the right atrium, right ventricle, and left ventricle in normal and abnormal hearts", *Circulation*, 33(6), (Jun. 1966), 933-944.

Bevan, J A, et al., "Postganglionic sympathetic delay in vascular smooth muscle", *Journal of Pharmacology & Experimental Therapeutics*, 152(2), (May 1966), 221-30.

Bevan, J. A., et al., "Sympathetic nerve-free vascular muscle", *Journal of Pharmacology & Experimental Therapeutics*, 157(1), (Jul. 1967), 117-124.

Bilgutay, A. M., "A new concept in the treatment of hypertension utilizing an implantable electronic device: "Baropacer"", *Trans Am Soc Artif Intern Organs.*, 10, (1964), 387-395.

Bilgutay, A. M., "Vagal tuning for the control of supraventricular arrhythmias", *Surgical Forum*, 16, (1965), 151-153.

Bilgutay, A. M, "Vagal tuning. A new concept in the treatment of supraventricular arrhythmias, angina pectoris, and heart failure", *Journal of Thoracic and Cardiovascular Surgery*, 56(1), (Jul. 1968), 71-82.

Borst, C., "Optimal frequency of carotid sinus nerve stimulation in treatment of angina pectoris", *Cardiovascular Research*, 8(5), (Sep. 1974), 674-80.

Braunwald, E., "Carotid sinus nerve stimulation in the treatment of angina pectoris and supraventricular tachycardia", *California Medicine*, 112(3), (Mar. 1970), 41-50.

Braunwald, E., "Relief of angina pectoris by electrical stimulation of the carotid-sinus nerves", *New England Journal of Medicine*, 277(24), (Dec. 14, 1967), 1278-1283.

Chapleau, M. W., "Contrasting effects of static and pulsatile pressure on carotid baroreceptor activity in dogs", *Circulation*, vol. 61, No. 5, (Nov. 1987), 648-658.

Chapleau, M. W., "Pulsatile activation of baroreceptors causes central facilitation of baroreflex", *American Journal Physiol Heart Circ Physiol* 256, (Jun. 1989), H1735-H1741.

Coleridge, J. C., et al., "Relationship between pulmonary arterial pressure and impulse activity in pulmonary arterial baroreceptor fibres", *Journal of Physiology*, 158, (Sep. 1961), 197-205.

Coleridge, J. C., "The distribution, connexions and histology of baroreceptors in the pulmonary artery, with some observations on the sensory innervation of the ductus arteriosus", *Journal of Physiology*, 156, (May 1961), 591-602.

Cooper, T. B, et al., "Neural effects on sinus rate and atrioventricular conduction produced by electrical stimulation from a transvenous electrode catheter in the canine right pulmonary artery", *Circulation Research*, vol. 46, No. 1, (Jan. 1980), 48-57.

Courtice, G. P., "Effect of frequency and impulse pattern on the non-cholinergic cardiac response to vagal stimulation in the toad, Bufo marinus", *Journal of the Autonomic Nervous System*, 48(3), (Aug. 1994), 267-272.

Dart Jr., C. H., "Carotid sinus nerve stimulation treatment of angina refractory to other surgical procedures", *Annals of Thoracic Surgery*, 11(4), (Apr. 1971), 348-359.

De Landsheere, D., "Effect of spinal cord stimulation on regional myocardial perfusion assessed by positron emission tomography", *American Journal of Cardiology*, 69(14), (May 1, 1992), 1143-1149.

Dunning, A. J., "Electrostimulation of the Carotid Sinus Nerve in Angina Pectoris", *University Department of Medicine*, Binnengasthuis, Amsterdam; Printed by Royal VanGorcum, Assen, Netherlands, (1971), 1-92.

Epstein, S. E., "Treatment of angina pectoris by electrical stimulation of the carotid-sinus nerves", *New England Journal of Medicine*, 280(18), (May 1, 1969), 971-978.

Farrehi, C., "Stimulation of the carotid sinus nerve in treatment of angina pectoris", *American Heart Journal*, 80(6), (Dec. 1970), 759-65.

Feliciano, L., "Vagal nerve stimulation releases vasoactive intestinal peptide which significantly increases coronary artery blood flow", *Cardiovascular Research*, 40(1), (Oct. 1998), 45-55.

Fromer, M., "Ultrarapid subthreshold stimulation for termination of atrioventricular node reentrant tachycardia", *Journal of the American College of Cardiology*, 20(4), (Oct. 1992), 879-83.

Grassi, Guido, et al., "Baroreflex and non-baroreflex modulation of vagal cardiac control after myocardial infarction", *Am J Cardiol.*, 84(5), (Sep. 1, 1999), 525-9.

Griffith, L. S..C., et al., "Electrical Stimulation of the Carotid Sinus Nerve in Normotensive and Renal Hypertensive Dogs", *Circulation*, 28, (Jul.-Dec. 1963), p. 730.

Henning, R. J., "Effects of autonomic nerve stimulation, asynchrony, and load on dP/dtmax and on dP/dtmin", *American Journal of Physiology*, 260(4 Pt 2), (Apr. 1991), H1290-H1298.

Henning, R. J., "Vagal nerve stimulation increases right ventricular contraction and relaxation and heart rate", *Cardiovascular Research*, 32(5), (Nov. 1996), 846-53.

Henning, R. J., "Vagal stimulation attenuates sympathetic enhancement of left ventricular function", *American Journal of Physiology*, 258(5 Pt 2), (May 1990), H1470-5.

Hood JR., W. B., et al., "Asynchronous contraction due to late systolic bulging at left ventricular pacing sites", *American Journal of Physiology*, 217(1), (Jul. 1969), 215-21.

Ishise, H., "Time course of sympathovagal imbalance and left ventricular dysfunction in conscious dogs with heart failure", *Journal of Applied Physiology*, 84(4), (Apr. 1998), 1234-41.

Jessurun, G. A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642, (Oct. 15, 1998), 921-926.

Kandel, E. R, et al., "Part VII: Arousal, Emotion, and Behavioral Homeostasis", In: *Principles of neural science*, New York : McGraw-Hill, Health Professions Division, (2000), 966-969.

Karpawich, P P, et al., "Altered cardiac histology following apical right ventricular pacing in patients with congenital atrioventricular block", *Pacing Clin Electrophysiol.*, 22(9), (Sep. 1999), 1372-1377.

Leclercq, C., et al., "Hemodynamic importance of preserving the normal sequence of ventricular activation in permanent cardiac pacing", *Am Heart J.*, 129(6), (Jun. 1995), 1133-1141.

Levy, M. N., et al., "Effects of Repetitive Bursts of Vagal Activity on Heart Rate", *Circulation Research*, 30(2), (1972), 186-195.

Li, M., "Vagal nerve stimulation markedly improves long-term survival after chronic heart failure in rats", *Circulation*, 109(1), (2004), 120-124.

Libbus, I., "Combined Remodeling Control Therapy and Anti-Remodeling Therapy by Implantable Cardiac Device", U.S. Appl. No. 10/850,341, filed May 20, 2004, 25 pgs.

Libbus, I., et al., "System and Method for Closed-Loop Neural Stimulation", U.S. Appl. No. 10/992,319, filed Nov. 18, 2004, 50 pgs.

Libbus, Imad, "Cardiac Rhythm Management Device With Neural Sensor", U.S. Appl. No. 10/992,320, filed Nov. 18, 2004, 65 pgs.

Libbus, Imad, "Implantable Device for Treating Epilepsy and Cardiac Rhythm Disorders", U.S. Appl. No. 11/312,178, filed Dec. 21, 2005, 39 pgs.

Libbus, Imad, "Method and Apparatus for Simultaneously Presenting Cardiac and Neural Signals", U.S. Appl. No. 11/114,246, filed Apr. 25, 2005, 58 Pgs.

Libbus, Imad, et al., "Method and Apparatus for Synchronizing Neural Stimulation to Cardiac Cycles", U.S. Appl. No. 11/099,141, filed Apr. 5, 2005, 36 pgs.

Libbus, Imad, "Neural Stimulation With Avoidance of Inappropriate Stimulation", U.S. Appl. No. 11/000,249, filed Nov. 30, 2004, 45 pgs.

Libbus, Imad, "Stimulator for Auricular Branch of Vagus Nerve", U.S. Appl. No. 11/005,703, filed Dec. 7, 2004, 35 pgs.

Libbus, Imad, "System and Method for Sustained Baroreflex Stimulation", U.S. Appl. No. 10/962,845, filed Oct. 12, 2004, 50 pgs.

Libbus, Imad, "System and Method to Deliver Therapy in Presence of Another Therapy", U.S. Appl. No. 11/125,503, filed May 10, 2005, 39 pgs.

Libbus, Imad, "System to Provide Myocardial and Neural Stimulation", U.S. Appl. No. 11/087,935, filed Mar. 23, 2005, 52 pgs.

Mannheimer, C, "Epidural spinal electrical stimulation in severe angina pectoris", *British Heart Journal*, 59(1), (Jan. 1988), 56-61.

Mannheimer, C, "Transcutaneous electrical nerve stimulation (TENS) in angina pectoris", *Pain*, 26(3), (Sep. 1986), 291-300.

Mannheimer, C, "Transcutaneous electrical nerve stimulation in severe angina pectoris", *European Heart Journal*3(4), (Aug. 1982), 297-302.

Martin, P., "Time-dependent heart period and contractility responses to successive brief vagal stimuli", *Am J Physiol*, 239(4), (Oct. 1980), H494-H500.

Mazgalev, T. N., "Autonomic modification of the atrioventricular node during atrial fibrillation: role in the slowing of ventricular rate", *Circulation*, 99(21), (Jun. 1, 1999), 2806-2814.

McCabe, Aaron, "Wireless ECG in Implantable Devices", U.S. Appl. No. 10/795,126, filed Mar. 5, 2004, 48 pgs.

Millar-Craig, M W, et al., "Circadian variation of blood-pressure", *Lancet*, 1(8068), (Apr. 15, 1978), 795-797.

Minisi, A J, et al., "Regional left ventricular deafferentation increases baroreflex sensitivity following myocardial infarction", *Cardiovasc Res.*, 58(1), (Apr. 1, 2003), 136-141.

Moffitt, Julia, "Combined Neural Stimulation and Cardiac Resynchronization Therapy", U.S. Appl. No. 11/078,460, filed Mar. 11, 2005, 35 pgs.

Murphy, D F, "Intractable angina pectoris: management with dorsal column stimulation", *Medical Journal of Australia*, 146(5), (Mar. 2, 1987), 260.

Neistadt, A, "Effects of electrical stimulation of the carotid sinus nerve in reversal of experimentally induced hypertension", *Surgery*, 61(6), (Jun. 1967), 923-31.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Pastore, Joseph M., et al., "Multi-Site Ventricular Pacing Therapy With Parasympathetic Stimulation", U.S. Appl. No. 10/700,368, filed Nov. 3, 2003, 18 pgs.

Peters, T K, "Temporal and spatial summation caused by aortic nerve stimulation in rabbits. Effects of stimulation frequencies and amplitudes", *Journal of the Autonomic Nervous System*, 27(3), (Aug. 1989), 193-205.

Peters, T K, "The principle of electrical carotid sinus nerve stimulation: a nerve pacemaker system for angina pectoris and hypertension therapy", *Annals of Biomedical Engineering*, 8(4-6), (1980), 445-58.

Philbin, D M, "Inappropriate shocks delivered by an ICD as a result of sensed potentials from a transcutaneous electronic nerve stimulation unit", *Pacing & Clinical Electrophysiology*, 21(10), (Oct. 1998), 2010-2011.

Prakash, P, "Asymmetrical distribution of aortic nerve fibers in the pig", *Anat Rec.*, 158(1), (May 1967), 51-57.

Rosenqvist, M, "The effect of ventricular activation sequence on cardiac performance during pacing", *Pacing and Electrophysiology*, 19(9), (1996), 1279-1286.

Rushmer, Robert F, "Chapter 5—Systemic Arterial Pressure", *In: Cardiovascular dynamics*, Philadelphia : Saunders, (1976), 176-216.

Schauerte, P, "Catheter stimulation of cardiac parasympathetic nerves in humans: a novel approach to the cardiac autonomic nervous system", *Circulation*, 104(20), (Nov. 13, 2001), 2430-2435.

Schauerte, P, "Ventricular rate control during atrial fibrillation by cardiac parasympathetic nerve stimulation: a transvenous approach", *Jorunal of the American College of Cardiology*, 34(7), (Dec. 1999), 2043-2050.

Schauerte, P. N., et al., "Transvenous parasympathetic cardiac nerve stimulation: an approach for stable sinus rate control", *Journal of Cardiovascular Electrophysiology*, 10(11), (Nov. 1999), 1517-1524.

Schauerte, P. N, "Transvenous Parasympathetic Nerve Stimulation in the Inferior Vena Cava and Atrioventricular Conduction", *Journal of Cardiovascular Electrophysiology*, 11(1), (Jan. 2000), 64-69.

Scherlag, M. A., "Endovascular Nerual Stimulation Via a Novel Basket Electrode Catheter: Comparison of Electrode Configurations", *Journal of Interventional Cardiac Electrophysiology*, 4(1), (Apr. 2000), 219-224.

Sigurdsson, A., et al., "The Role of Neurohormonal Activation in Chronic Heart Failure and Postmyocardial Infarction", *American Heart Journal*, 132(1, Part 2), (Jul. 1996), 229-234.

Takahashi, N., "Vagal modulation of ventricular tachyarrhythmias induced by left ansae subclaviae stimulation in rabbits", *Japanese Heart Journal*, 39(4), (Jul. 1998), 503-511.

Tse, H. F., et al., "Long-term effect of right ventricular pacing on myocardial perfusion and function", *J Am Coll Cardiol.*, 29(4), (Mar. 15, 1997), 744-749.

Vanoli, E., et al., "Vagal Stimulation and Prevention of Sudden Death in Conscious Dogs with a Healed Myocardial Infarction", *Circulation Research*, 68(5), (1991), 1471-1481.

Veerman, D. P., et al., "Circadian profile of systemic hemodynamics", *Hypertension*, 26(1), (Jul. 1995), 55-59.

Verity, M. A., et al., "Plurivesicular nerve endings in the pulmonary artery", *Nature*, 211(48), (Jul. 30, 1966), 537-538.

Verity, M., et al., "Pulmonary artery innervation: a morphopharmacologic correlation", *Proceedings of the Western Pharmacology Society*, 8, (1965), 57-59.

Wallick, D. W., "Selective AV nodal vagal stimulation improves hemodynamics during acute atrial fibrillation in dogs", *American Journal of Physiology—Heart & Circulatory Physiology* 281(4), (Oct. 2001), H1490-1497.

Waninger, M. S., "Electrophysiological control of ventricular rate during atrial fibrillation", *Pacing & Clinical Electrophysiology*, 23(8), (Aug. 2000), 1239-1244.

Wiggers, C. J., et al., "The muscular reactions of the mammalian ventricles to artificial surface stimuli", *American Journal of Physiology*, (1925), 346-378.

Zhang, Y., "Optimal ventricular rate slowing during atrial fibrillation by feedback AV nodal-selective vagal stimulation", *American Journal of Physiology—Heart & Circulatory Physiology*, 282(3), (Mar. 2002), H1102-H1110.

Zhou, X., "Prevention of high incidence of neurally mediated ventricular arrhythmias by afferent nerve stimulation in dogs", *Circulation*, 101(7), (Feb. 22, 2000), 819-824.

"U.S. Appl. No. 11/459,481, Non-Final Office Action mailed May 28, 2009", 10 pgs.

"U.S. Appl. No. 12/986,762, Restriction Requirement mailed Dec. 5, 2012", 6 pgs.

"U.S. Appl. No. 13/198,477, Response filed Nov. 30, 2012 to Non Final Office Action mailed Aug. 3, 2012", 9 pgs.

"U.S. Appl. No. 13/198,477, Restriction Requirement mailed Jun. 27, 2012", 8 pgs.

"Japanese Application Serial No. 2008-505371, Office Action mailed Mar. 12, 2012", w/ English Translation, 13 pgs.

"Japanese Application Serial No. 2008-505371, Response filed Jun. 8, 2012 to Office Action mailed Feb. 13, 2012", English Claims with response, 11 pgs.

\* cited by examiner

METHOD AND APPARATUS FOR SYNCHRONIZING NEURAL STIMULATION TO CARDIAC CYCLES

CROSS REFERENCE TO RELATED APPLICATION

This application is a divisional of U.S. application Ser. No. 11/099,141, filed Apr. 5, 2005, now issued as U.S. Pat. No. 7,542,800, which is hereby incorporated by reference in its entirety.

FIELD OF THE INVENTION

This document generally relates to neural stimulation systems and particularly to a system providing for synchronization of neural stimulation to cardiac cycles.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are accomplished by cyclic contractions of the myocardium (heart muscles). Each cycle, known as the cardiac cycle, includes systole and diastole. During systole, the heart ejects blood. During diastole, the heart is filled with blood for the next ejection (systolic) phase, and the myocardial tissue is perfused. In a normal heart, the sinoatrial node generates electrical impulses called action potentials. The electrical impulses propagate through an electrical conduction system to various regions of the heart to excite the myocardial tissue of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue result in systolic dysfunction—because the myocytes do not contract in unison—and diastolic dysfunction—because the myocytes do not relax in unison. Decreased systolic and diastolic performance each contribute to a poor overall hemodynamic performance, including a diminished blood supply to the heart and the rest of the body.

The hemodynamic performance is modulated by neural signals in portions of the autonomic nervous system. For example, the myocardium is innervated with sympathetic and parasympathetic nerves. Activities in these nerves, including artificially applied electrical stimuli, modulate the heart rate and contractility (strength of the myocardial contractions). Electrical stimulation applied to the sympathetic nerves is known to increase the heart rate and the contractility, shortening the systolic phase of a cardiac cycle, and lengthening the diastolic phase of the cardiac cycle. Electrical stimulation applied to the parasympathetic nerves is known to have essentially the opposite effects.

The ability of the electrical stimulation of the autonomic nerves in modulating the heart rate and contractility is utilized to treat abnormal cardiac conditions, such as to control myocardial remodeling and to prevent arrhythmias following myocardial infarction. It is observed that the effects of such electrical stimulation are dependent on timing of the delivery of electrical stimuli in relation to the cardiac cycle. Thus, it is desirable to synchronize the delivery of the electrical stimuli to the cardiac cycle. Because the electrical stimuli are delivered to portions of nerves external to the heart, there is a need for detecting a timing reference signal for synchronizing the delivery of the electrical stimuli to the cardiac cycle without intracardiac sensing.

SUMMARY

A neural stimulator senses a reference signal indicative of cardiac cycles each including a predetermined type timing reference event using a sensor external to the heart and blood vessels. The delivery of the neural stimulation pulses are synchronized to that timing reference event.

In one embodiment, a neural stimulation system includes a stimulation output circuit, a reference signal sensor, a reference event detection circuit, and a stimulation control circuit. The stimulation output circuit delivers neural stimulation pulses. The reference signal sensor senses a reference signal indicative of cardiac cycles each including a predetermined type timing reference event. The reference signal sensor may be placed in a site external to the circulatory system. The reference event detection circuit detects the predetermined type timing reference event. The stimulation control circuit controls the delivery of the neural stimulation pulses and includes a synchronization module. The synchronization module synchronizes the delivery of the neural stimulation pulses to the predetermined type timing reference event.

In one specific embodiment, the neural stimulation system includes a stimulation output circuit, one or more electrodes, a cardiac event detection circuit, and a stimulation control circuit. The stimulation output circuit delivers neural stimulation pulses. The one or more electrodes sense an electrocardiographic (ECG) signal. The cardiac event detection circuit detects predetermined type cardiac events from the ECG signal. The stimulation control circuit controls the delivery of the neural stimulation pulses and includes a synchronization module. The synchronization module synchronizes the delivery of the neural stimulation pulses to the predetermined type cardiac events.

In another specific embodiment, the neural stimulation system includes a stimulation output circuit, an acoustic sensor, a heart sound detection circuit, and a stimulation control circuit. The stimulation output circuit delivers neural stimulation pulses. The implantable acoustic sensor senses an acoustic signal indicative of heart sounds. The heart sound detection circuit detects predetermined type heart sounds using the acoustic signal. The stimulation control circuit controls the delivery of the neural stimulation pulses and includes a synchronization module. The synchronization module synchronizes the delivery of the neural stimulation pulses to the predetermined type heart sounds.

In another specific embodiment, the neural stimulation system includes a stimulation output circuit, a hemodynamic sensor, a hemodynamic event detection circuit, and a stimulation control circuit. The stimulation output circuit delivers neural stimulation pulses. The hemodynamic sensor senses a hemodynamic signal. The hemodynamic event detection circuit detects a predetermined type hemodynamic event using the hemodynamic signal. The stimulation control circuit controls the delivery of the neural stimulation pulses and includes a synchronization module. The synchronization module synchronizes the delivery of the neural stimulation pulses to the predetermined type hemodynamic event.

In one embodiment, a method for neural stimulation is provided. A timing reference signal is sensed using a reference signal sensor placed external to the circulatory system.

The timing reference signal is indicative of cardiac cycles each including a predetermined type timing reference event. The predetermined type timing reference event is detected from the reference signal. A delivery of neural stimulation pulses is synchronized to the detected timing reference event.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
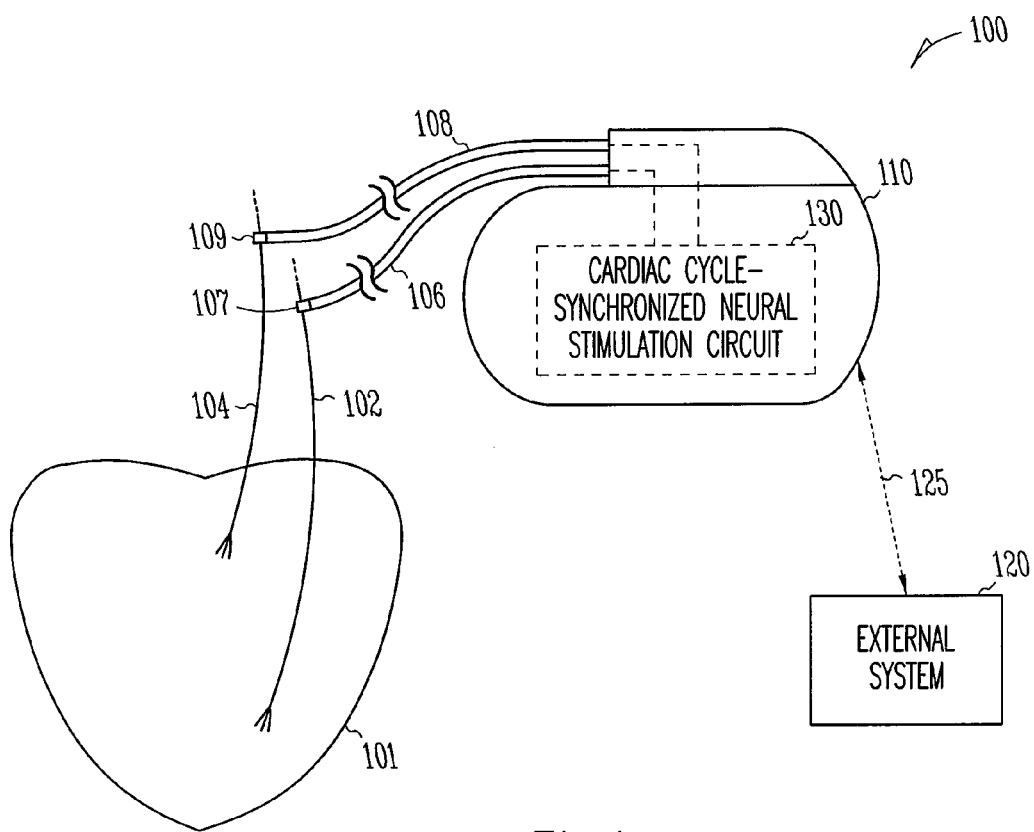
FIG. 1 is an illustration of an embodiment of a neural stimulation system and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a neural stimulation system that synchronizes the delivery of neural stimulation pulses to cardiac cycles. The neural stimulation system includes an implantable neural stimulator that senses a reference signal indicative of cardiac cycles each including a predetermined type timing reference event using an implantable reference event sensor. The implantable reference event sensor is an extracardiac and extravascular sensor, i.e., a sensor that is placed external to a patient's circulatory system including the heart and blood vessels. The delivery of the neural stimulation pulses are synchronized to the timing reference event. Examples of the reference signal include a wireless ECG, an acoustic signal indicative of heart sounds, and a hemodynamic signal.

In this document, "Surface ECG" refers to a cardiac electrical signal sensed with electrodes attached onto the exterior surface of the skin. "Wireless ECG" refers to a signal approximating the surface ECG, acquired without using surface (non-implantable, skin contact) electrodes. "Subcutaneous ECG" is a form of wireless ECG and includes a cardiac electrical signal sensed through electrodes implanted in subcutaneous tissue, such as through electrodes incorporated onto an implantable medical device that is subcutaneously implanted. As reflected in their corresponding morphologies, the surface ECG results from electrical activities of the entire heart. The wireless ECG, including but not being limited to the subcutaneous ECG, has a morphology that approximates that of the surface ECG and reflects electrical activities of a substantial portion of the heart, up to the entire heart.

In this document, an "acoustic signal" includes any signal indicative of heart sounds. "Heart sounds" include audible mechanical vibrations caused by cardiac activity that can be sensed with a microphone and audible and inaudible mechanical vibrations caused by cardiac activity that can be sensed with an accelerometer. Known type heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

In this document, a "hemodynamic signal" includes a signal providing for monitoring, calculation, or estimation of one or more measures of hemodynamic performance such as blood pressure or pressure-related parameters, cardiac output, stroke volume, volume of blood flow, change in (e.g., derivative of) the volume of blood flow, and/or velocity of blood flow.

FIG. 1 is an illustration of an embodiment of a neural stimulation system 100 and portions of an environment in which system 100 is used. System 100 includes implantable medical device 110 that delivers neural stimulation pulses through leads 106 and 108, an external system 120, and a telemetry link 125 providing for communication between implantable medical device 110 and external system 120. For illustrative purpose only, FIG. 1 shows that lead 106 includes an electrode 107 coupled to a nerve 102 of the sympathetic nervous system, and lead 108 includes an electrode 109 coupled a nerve 104 of the parasympathetic nervous system. Nerves 102 and 104 innervate a heart 101. In various embodiments, implantable medical device 110 provides neural stimulation to any one or more nerves through one or more leads for modulating one or more functions of the circulatory system including heart 101. Such leads include implantable neural leads each including at least one electrode for sensing neural activities and/or delivering neural stimulation pulses. One example of such an electrode includes a cuff electrode for placement around an aortic, carotid, or vagus nerve.

Implantable medical device 110 delivers the neural stimulation pulses and includes a cardiac cycle-synchronized neural stimulation circuit 130. Cardiac cycle-synchronized neural stimulation circuit 130 detects a predetermined type of timing reference event from a cardiac cycle and synchronizes the delivery of neural stimulation pulses to that timing reference event. In one embodiment, cardiac cycle-synchronized neural stimulation circuit 110 starts a predetermined offset time interval upon detection of the timing reference event and delivers a burst of neural stimulation pulses when the offset time interval expires. In one embodiment, implantable medical device 110 is capable of monitoring physiologic signals and/or delivering therapies in addition to the neural stimulation. Examples of such additional therapies include cardiac pacing therapy, cardioversion/defibrillation therapy, cardiac resynchronization therapy, cardiac remodeling control therapy, drug therapy, cell therapy, and gene therapy. In various embodiments, implantable medical device 110 delivers the neural stimulation in coordination with one or more such additional therapies.

External system 120 provides for control of and communication with implantable medical device 110 by a physician or other caregiver. In one embodiment, external system 120 includes a programmer. In another embodiment, external system 120 is a patient management system including an external device communicating with implantable medical device 110 via telemetry link 125, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 125 is an inductive telemetry link. In an alternative embodiment, telemetry link 125 is a far-field radio-frequency (RF) telemetry link. Telemetry link 125 provides for data transmission from implantable medical device 110 to external system 120. This includes, for example, transmitting real-time physiological data acquired by implantable medical device 110, extracting physiological data acquired by and stored in implantable medical device 110, extracting patient history data such as occurrences of arrhythmias and therapy deliveries recorded in implantable medical device 110, and/or extracting data indicating an operational status of implantable medical device 110 (e.g., battery status and lead impedance). Telemetry link 125 also provides for data transmission from external system 120 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies.

Figure 2:
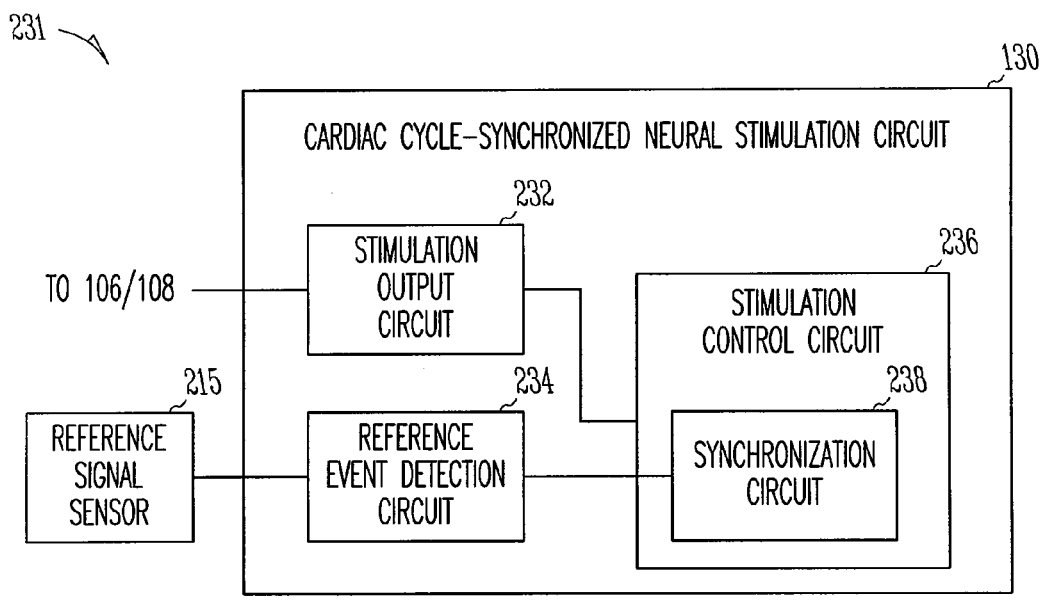
FIG. 2 is a block diagram illustrating an embodiment of a circuit of a cardiac cycle-synchronized neural stimulation system.

FIG. 2 is a block diagram illustrating an embodiment of a circuit of a cardiac cycle-synchronized neural stimulation system 231. System 231 includes a reference signal sensor 215 and cardiac cycle-synchronized neural stimulation circuit 130.

Reference signal sensor 215 senses a reference signal indicative of cardiac cycles each including a predetermined type timing reference event. In one embodiment, reference signal sensor 215 is an implantable reference signal sensor. The timing reference event is a recurring feature of the cardiac cycle that is chosen to be a timing reference to which the neural stimulation is synchronized. In one embodiment, reference signal sensor 215 is configured for extracardiac and extravascular placement, i.e., placement external to the heart and blood vessels. Examples of reference signal sensor 215 include a set of electrodes for sensing a subcutaneous ECG signal, an acoustic sensor for sensing an acoustic signal indicative of heart sounds, and a hemodynamic sensor for sensing a hemodynamic signal indicative of hemodynamic performance. In one embodiment, implantable medical device 110 has an implantable housing that contains both a reference signal sensor 215 and cardiac cycle-synchronized neural stimulation circuit 130. In another embodiment, reference signal sensor 215 is incorporated onto the housing of implantable medical device 110. In another embodiment, reference signal sensor 215 is electrically connected to implantable medical device 110 through one or more leads. In another embodiment, reference signal sensor 215 is communicatively coupled to implantable medical device 110 via an intra-body telemetry link.

Cardiac cycle-synchronized neural stimulation circuit 130 includes a stimulation output circuit 232, a reference event detection circuit 234, and a stimulation control circuit 236. Reference event detection circuit 234 receives the reference signal from reference signal sensor 215 and detects the timing reference event from the reference signal. Stimulation control circuit 236 controls the delivery of the neural stimulation pulses and includes a synchronization module 238. Synchronization module 238 receives a signal indicative of the detection of each timing reference event and synchronizes the delivery of the neural stimulation pulses to the detected timing reference event. Stimulation output circuit 232 delivers neural stimulation pulses upon receiving a pulse delivery signal from stimulation control circuit 236.

Figure 3:
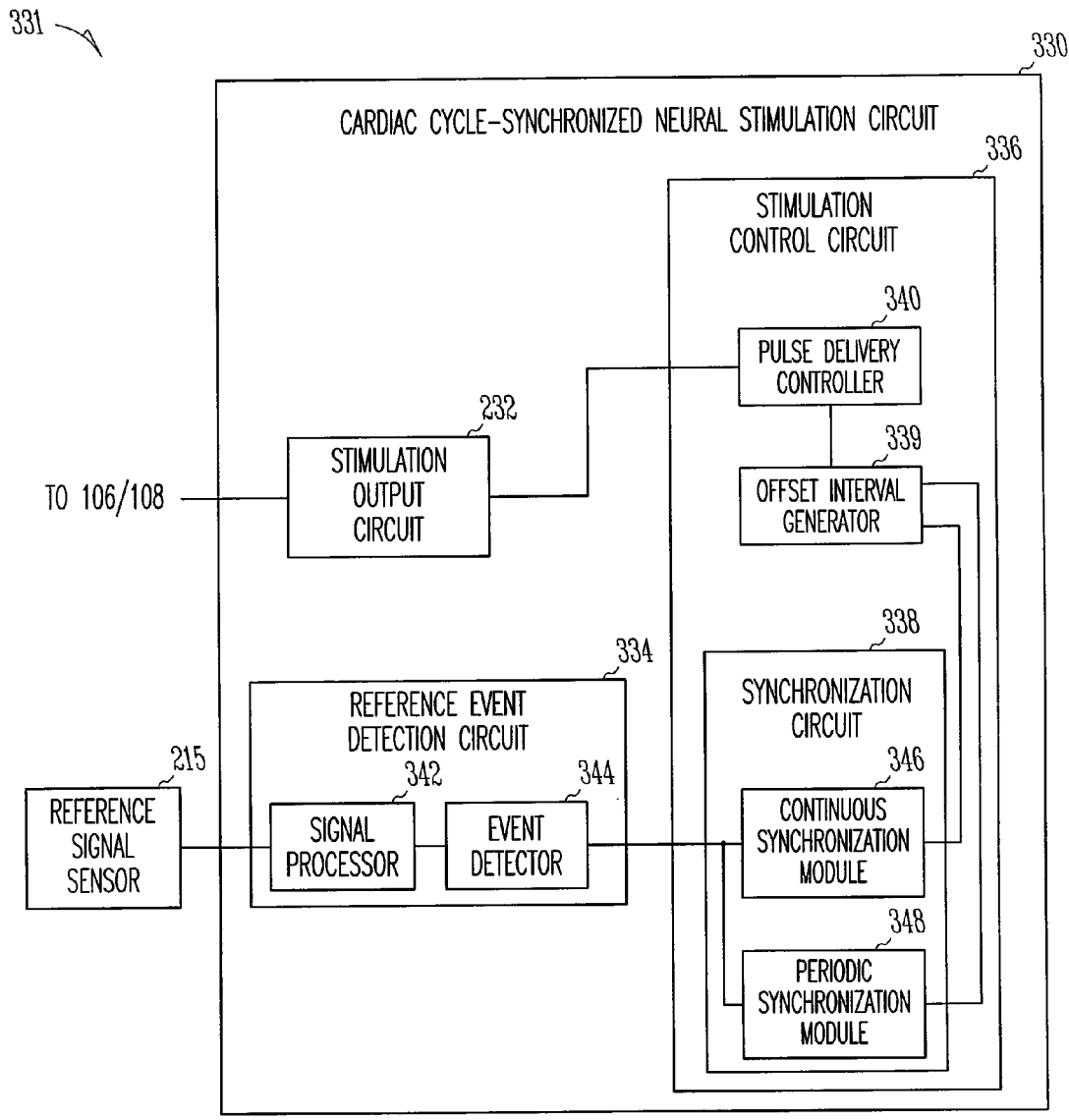
FIG. 3 is a block diagram illustrating a specific embodiment of the circuit of FIG. 2.

FIG. 3 is a block diagram illustrating an embodiment of a circuit of a cardiac cycle-synchronized neural stimulation system 331, which is a specific embodiment of system 231. System 331 includes reference signal sensor 215 and a cardiac cycle-synchronized neural stimulation circuit 330, which is a specific embodiment of cardiac cycle-synchronized neural stimulation circuit 130. Cardiac cycle-synchronized neural stimulation circuit 330 includes stimulation output circuit 232, a reference event detection circuit 334, and a stimulation control circuit 336.

Reference event detection circuit 334 is a specific embodiment of reference event detection 234 and includes a signal processor 342 and an event detector 344. Signal processor 342 receives the reference signal sensed by reference signal sensor 215 and processes the reference signal in preparation for the detection of the timing reference events by event detector 344. Event detector 344 includes a comparator having an input to receive the processed reference signal, another input to receive a detection threshold, and an output producing a detection signal indicating a detection of the timing reference signal. In one embodiment, signal processor 342 processes the reference signal to provide for extraction of the timing reference event based on a single cardiac cycle. In one specific embodiment, signal processor 342 includes a filter having a pass-band corresponding to a frequency range of the timing reference event to prevent unwanted activities in the reference signal from being detected by event detector 344. In another specific embodiment, signal processor 342 includes a blanking period generator to generate a blanking period that blanks the unwanted activities in the reference signal. This approach is applied when an approximate timing relationship between the timing reference event and the unwanted activities, or an approximate timing relationship between another detectable event and the unwanted activities, is predictable. In another specific embodiment, the blanking period generator generates a blanking period that blanks cardiac pacing artifacts in the reference signal, i.e., unwanted activities caused by delivery of cardiac pacing pulses. In another specific embodiment, signal processor 342 includes a timing interval generator to generate a timing interval between an intermediate event and the timing reference event. This approach is applied when the intermediate event is more easily detectable than the timing reference event and when an approximate timing relationship between the intermediate event and the timing reference event is predictable. In another embodiment, signal processor 342 processes the reference signal to provide for extraction of the timing reference event based on a plurality of cardiac cycles. In one specific embodiment, signal processor 342 includes a signal averaging circuit that averages the reference signal over a predetermined number of cardiac cycles before the detection of the timing reference event by event detector 344.

Stimulation control circuit 336 is a specific embodiment of stimulation control circuit 236 and includes a synchronization circuit 338, an offset interval generator 339, and a pulse delivery controller 340. Synchronization circuit 338 includes one or both of a continuous synchronization module 346 and a periodic synchronization module 348. Continuous synchronization module 346 synchronizes the delivery of the neural stimulation pulses to the timing reference event of consecutive cardiac cycles. Periodic synchronization module 348 synchronizes the delivery of the neural stimulation pulses to the timing reference event of selected cardiac cycles on a periodic basis. Offset interval generator 339 produces an offset interval starting with the detected timing reference event. Pulse delivery controller 340 sends the pulse delivery signal to start a delivery of a burst of a plurality of neural stimulation pulses when the offset interval expires. In one embodiment, pulse delivery controller 340 sends the pulse delivery signal after the detection of the timing reference event for each of consecutive cardiac cycles. In another embodiment, pulse delivery controller 340 sends the pulse delivery signal after the detection of the timing reference event for selected cardiac cycles according to a predetermined pattern or schedule, such as on a periodic basis.

Figure 4:
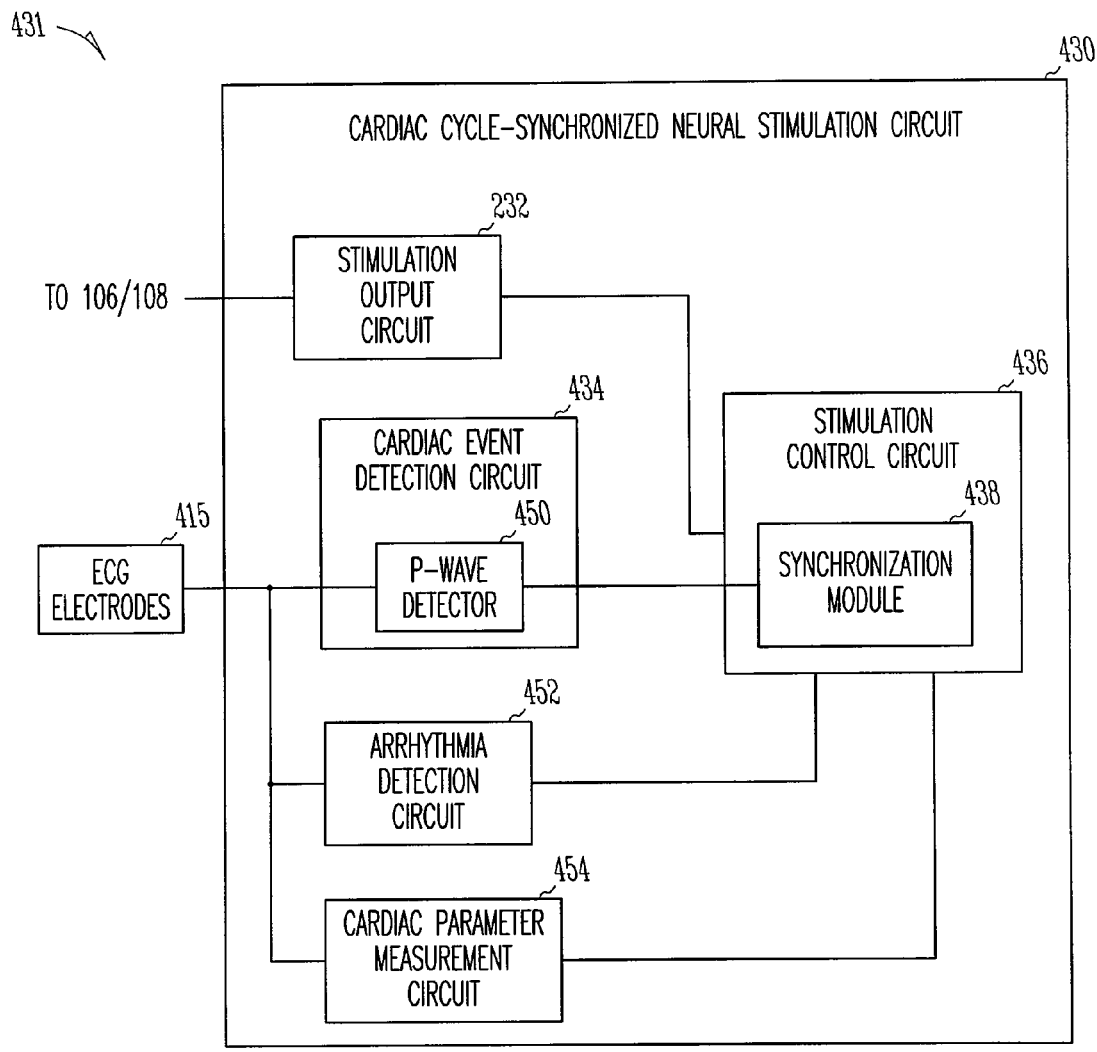
FIG. 4 is a block diagram illustrating an embodiment of a circuit using a wireless ECG to synchronize neural stimulation to cardiac cycles.

FIG. 4 is a block diagram illustrating an embodiment of a cardiac cycle-synchronized neural stimulation system 431, which is a specific embodiment of system 231 and uses a wireless ECG to synchronize neural stimulation to cardiac cycles. System 431 includes ECG electrodes 415 and a cardiac cycle-synchronized neural stimulation circuit 430, which is a specific embodiment of cardiac cycle-synchronized neural stimulation circuit 230. Cardiac cycle-synchronized neural stimulation circuit 430 includes stimulation output circuit 232, a cardiac event detection circuit 434, an arrhythmia detection circuit 452, a cardiac parameter measurement circuit 454, and a stimulation control circuit 436.

In one embodiment, ECG electrodes 415 include surface ECG electrodes. In another embodiment, ECG electrodes 415 include electrodes for sensing a wireless ECG signal. In one embodiment, ECG electrodes 415 include subcutaneous electrodes for sensing a subcutaneous ECG signal. In one embodiment, the subcutaneous electrodes are incorporated onto the implantable medical device 110, which is to be subcutaneously implanted. Examples of such subcutaneous electrodes are discussed below with reference to FIG. 5. In one embodiment, at least one subcutaneous electrode is placed in a selected location in the body near the base of the heart to allow selective detection of atrial depolarizations (P-waves). In another embodiment, multiple subcutaneous electrodes are placed near base and apex of the heart to allow P-wave detection by subtracting out unwanted activities including ventricular depolarizations (R-waves). This approach applies when it is difficult to isolate P-waves by selecting electrode sites and filtering. At least one subcutaneous electrode is placed near the apex of the heart to allow detection of R-waves. The detected R-waves are then used to isolate, by subtraction, P-waves from a subcutaneous ECG signal that includes both P-waves and R-waves.

Cardiac event detection circuit 434 is a specific embodiment of reference event detection circuit 234. In one embodiment, cardiac event detection circuit 434 includes a signal processor such as signal processor 342 and an event detector such as event detector 344. The signal processor includes a wireless ECG sensing circuit to amplify and filter the subcutaneous ECG signal sensed through ECG electrodes 415. An example of electrodes and a circuit for sensing wireless ECG signals including subcutaneous ECG signals is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated herein by reference in its entirety. In one embodiment, as illustrated in FIG. 4, the timing reference event is a P-wave. Cardiac event detection circuit 434 includes a P-wave detector 450 to detect P-waves from the wireless ECG signal. In one specific embodiment, P-wave detector 450 includes a filter having a pass-band corresponding to a frequency range of P-waves. In another specific embodiment, P-wave detector 450 includes an R-wave detector to detect R-waves from one subcutaneous signal and a blanking period generator to generate blanking periods to blank unwanted activities including the R-waves in another wireless ECG signal. In another specific embodiment, P-wave detector 450 includes an R-wave detector to detect R-waves from the subcutaneous signal and a timing interval generator to generate a timing interval upon detection of each R-wave. A P-wave is estimated to occur at the end of the timing interval.

Arrhythmia detection circuit 452 and cardiac parameter measurement circuit 454 provide for control of neural stimulation based on cardiac conditions. Arrhythmia detection circuit 452 detects one or more types of arrhythmia from the wireless ECG signal. Cardiac parameter measurement module 454 measures one or more cardiac parameters such as a heart rate and an atrioventricular interval from the wireless ECG signal.

Stimulation control circuit 436 is a specific embodiment of stimulation control circuit 336 and includes a synchronization module 438. Synchronization module 438 synchronizes the delivery of the neural stimulation pulses to the detected cardiac events such as P-waves. In one embodiment, stimulation control circuit 436 includes elements corresponding to those of stimulation circuit 336, including offset interval generator 339 and pulse delivery controller 340. Synchronization circuit 438 includes one or both of a continuous synchronization module to synchronize the delivery of the neural stimulation pulses to the P-wave of each of consecutive cardiac cycles and a periodic synchronization module to synchronize the delivery of the neural stimulation pulses to the P-wave of each of selected cardiac cycles on a periodic basis. The offset interval generator produces an offset interval starting with each detected P-wave. The pulse delivery controller sends the pulse delivery signal to start a delivery of a burst of a plurality of neural stimulation pulses when the offset interval expires. In one embodiment, the pulse delivery controller sends the pulse delivery signal after the detection of the P-wave for each of consecutive cardiac cycles. In another embodiment, the pulse delivery controller sends the pulse delivery signal after the detection of the P-wave for each of selected cardiac cycles according to a predetermined pattern or schedule, such as on a periodic basis.

In one embodiment, stimulation control circuit 436 also controls the delivery of the neural stimulation pulses based on the cardiac rhythm detected by arrhythmia detection circuit 452 and/or the cardiac parameters measured by cardiac parameter measurement circuit 454. In one embodiment, stimulation control circuit 436 withholds or adjusts the delivery of the neural stimulation pulses when an arrhythmia is detected. In another embodiment, stimulation control circuit 436 starts, stops, or adjusts the delivery of the neural stimulation pulses based on the measured cardiac parameter, such as the heart rate and the atrioventricular interval.

Figure 5:
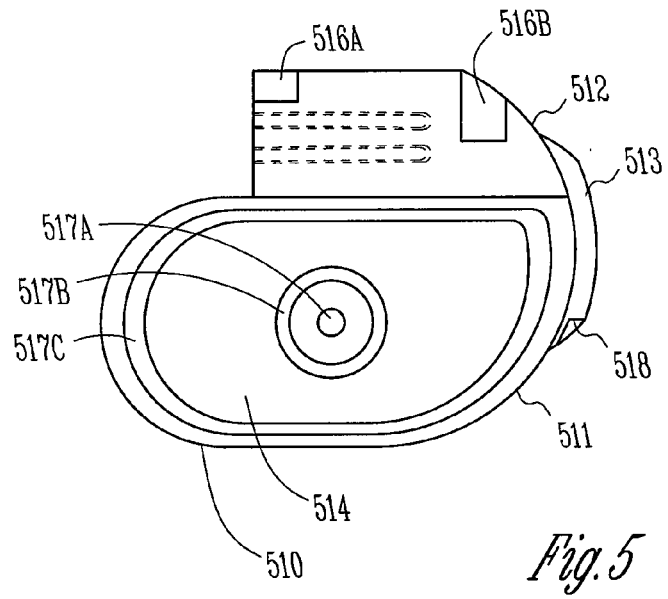
FIG. 5 is an illustration of an embodiment of an electrode system for subcutaneous ECG sensing.

FIG. 5 is an illustration of an embodiment of an electrode system for sensing one or more subcutaneous ECG signals. An electrode system for subcutaneous ECG sensing includes two or more implantable electrodes. These implantable electrodes are selected from the electrodes including, but not being limited to, those illustrated in FIG. 5. The electrodes are selected to allow for sensing electrical activities from a substantial portion of the heart, up to the entire heart. FIG. 5 shows an implantable medical device 510, which is a specific embodiment of implantable medical device 110, and electrodes incorporated onto that device. Implantable medical device 510 is to be subcutaneously implanted in a patient in need of neural stimulation to modulate cardiac functions. In one embodiment, ECG electrodes 415 include one or more electrodes shown in FIG. 5. In another embodiment, in addition to one or more electrodes shown in FIG. 5, ECG electrodes 415 include one or more electrodes each electrically connected to implantable medical device 510 through a lead.

Implantable medical device 510 includes a hermetically sealed can 511 to house its circuit. Can 511 has an outer surface subject to contact with body tissue. Can 511 includes or provides for a base of a can electrode 514 that is selectable as one of the electrodes for sensing a subcutaneous ECG signal. At least a portion of the outer surface of can 511 is made of electrically conductive material. In one embodiment, can 511 is used as can electrode 514. In one specific embodiment, can electrode 514 includes at least one conductive portion of can 511. In another embodiment, can electrode 514 is incorporated onto the outer surface of can 511 and is electrically insulated from any conductive portion of can 511 using a non-conductive layer. In one specific embodiment, a hermetically sealed feedthrough including a conductor provides for an electrical connection between can electrode 514 and the circuit housed in can 511.

A header 512 is attached to can 511 and includes connectors providing for electrical access to the circuit housed in can 511. In one embodiment, one or more of header electrodes 516A-B are incorporated into the header. Header electrodes 516A-B are each selectable as one of the electrodes for sensing a subcutaneous ECG signal.

In one embodiment, two or more concentric electrodes 517A-C are incorporated onto the outer surface of can 511. Each of the concentric electrodes 517A-C is selectable as one of the electrodes for sensing a subcutaneous ECG signal. Concentric electrodes 517A-C are insulated from the conductive portion of can 511 with a non-conductive layer and connected to the circuit housed in can 511 via hermetically sealed feedthroughs. In one embodiment, two electrodes, including an inner electrode and an outer electrode, are selected from concentric electrodes 517A-C for the wireless ECG sensing. In one embodiment, the outer electrode has a ring shape. In another embodiment, the outer electrode has a shape approaching the contour of can 511.

In one embodiment, implantable medical device 510 includes an antenna 513 used for a far-field RF telemetry link providing for communication between implantable medical device 510 and external system 120. Antenna 513 is electrically connected to the circuit housed in can 511. In one embodiment, antenna 513 projects from header 512 and extends along one side of can 511. In one embodiment, antenna 513 includes a metal conductor with a distal portion exposed for functioning as an antenna electrode 518, which is selectable as one of the electrodes for sensing a subcutaneous ECG signal.

It is to be understood that the electrodes illustrated in FIG. 5 are intended to be examples but not limitations. Other electrode configurations are usable as long as they provide for sensing of surface ECG signals or signals that approximate the surface ECG or otherwise allows for detection of a timing reference signal for synchronizing the delivery of neural stimulation pulses to cardiac cycles. In various embodiments in which multiple subcutaneous ECG vectors are sensed, multiple pairs of electrodes are selected, simultaneously or one at a time, for a multi-channel (multi-vector) subcutaneous ECG sensing. In one specific embodiment, one or more of subcutaneous ECG vectors are sensed to approximate one or more vectors of a standard multi-lead surface ECG recording. In another specific embodiment, multiple subcutaneous ECG vectors are sensed based on needs of specific information for synchronizing the delivery of neural stimulation pulses to cardiac cycles. Such subcutaneous ECG vectors do not necessarily approximate standard surface ECG vectors. In one specific embodiment, implantable medical device 510 includes header electrodes 516A-B and can electrode 514 for the subcutaneous ECG sensing. Implantable medical device 510 is programmable for sensing subcutaneous ECG vectors between (1) header electrodes 516A and 516B, (2) header electrode 516A and can electrode 514, and/or (3) header electrode 516B and can electrode 514. In another specific embodiment, implantable medical device 510 includes one of header electrodes 516A-B, antenna electrode 518, and can electrode 514 for the subcutaneous ECG sensing. Implantable medical device 510 is programmable for sensing subcutaneous ECG vectors between (1) header electrode 516A or 516B and antenna electrode 518, (2) header electrode 516A or 516B and can electrode 514, and/or (3) antenna electrode 518 and can electrode 514. In another specific embodiment, implantable medical device 510 includes header electrodes 516A-B, antenna electrode 518, and can electrode 514 for the subcutaneous ECG sensing. Implantable medical device 510 is programmable for sensing subcutaneous ECG vectors between (1) header electrodes 516A and 518, (2) header electrode 516A and antenna electrode 518, (3) header electrode 516A and can electrode 514, (4) header electrode 516B and antenna electrode 518, (5) header electrode 516B and can electrode 514, and/or (6) antenna electrode 518 and can electrode 514. Other specific embodiments involving any electrode combinations for the subcutaneous ECG sensing will be employed based on needs and consideration for synchronizing the delivery of neural stimulation pulses to cardiac cycles as well as needs and considerations for performing other diagnostic and/or therapeutic functions provided by implantable medical device 510.

The selection of subcutaneous ECG vectors depends on the purpose for the subcutaneous ECG sensing. When the subcutaneous ECG signal is sensed for detecting P-waves, the subcutaneous ECG vector that provide for a reliable P wave detection are selected. When the subcutaneous ECG signal is sensed for detecting R-waves, one or more subcutaneous ECG vectors that provide for a reliable R wave detection are selected. In one embodiment, when more than one subcutaneous ECG vector provides for a reliable sensing for a particular purpose, the subcutaneous ECG vector showing the highest signal-to-noise ratio (SNR) for that purpose is selected. For example, if the subcutaneous ECG is sensed for detecting P waves, the subcutaneous ECG vector showing the highest SNR with P waves being considered as the signal that is selected.

Figure 6:
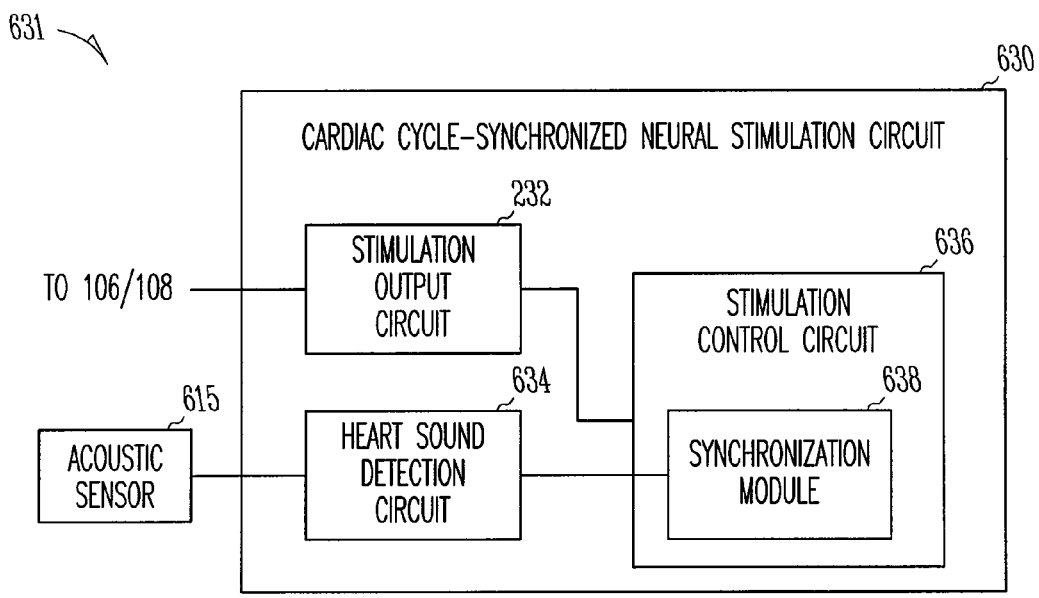
FIG. 6 is a block diagram illustrating an embodiment of a circuit using heart sounds to synchronize neural stimulation to cardiac cycles.

FIG. 6 is a block diagram illustrating an embodiment of a cardiac cycle-synchronized neural stimulation system 631, which is a specific embodiment of system 231 and uses heart sounds to synchronize neural stimulation to cardiac cycles. System 631 includes an acoustic sensor 615 and a cardiac cycle-synchronized neural stimulation circuit 630, which is a specific embodiment of cardiac cycle-synchronized neural stimulation circuit 230. Cardiac cycle-synchronized neural stimulation circuit 630 includes stimulation output circuit 232, a heart sound detection circuit 634, and a stimulation control circuit 636.

Acoustic sensor 615 senses an acoustic signal indicative heart sounds. In one embodiment, acoustic sensor 615 includes an implantable acoustic sensor. In one embodiment, acoustic sensor 615 includes an accelerometer. In another embodiment, acoustic sensor 615 includes a microphone. In one specific embodiment, acoustic sensor 615 is included in implantable medical device 110. In another specific embodiment, acoustic sensor 615 is incorporated onto a lead connected to implantable medical device 110.

Heart sound detection circuit 634 detects predetermined type heart sounds from the acoustic signal. Heart sound detection circuit 634 includes one or more of a first heart sound (S1) detector to detect S1, a second heart sound (S2) detector to detect S2, a third heart sound (S3) detector to detect S3, and a fourth heart sound (S4) detector to detect S4. In one embodiment, the type of heart sounds to be detected is determined based on whether each particular type of heart sounds is consistently recurring and reliably detectable in an individual patient. In one embodiment, cardiac event detection circuit 634 includes a signal processor such as signal processor 342 and an event detector such as event detector 344. In one specific embodiment, heart sound detection circuit 634 includes a filter having a pass-band corresponding to a frequency range of the predetermined type heart sounds. In another specific embodiment, heart sound detection circuit 634 includes a signal averaging circuit to average the acoustic signal over a predetermined number of cardiac cycles before the detection of the predetermined type heart sounds. In another specific embodiment, heart sound detection circuit 634 receives an activity signal indicative of the patient's gross physical activity level and stops detecting heart sounds while the activity signal exceeds a predetermined threshold activity level. In another embodiment, heart sound detection circuit 634 includes an S2 detector and/or an S3 detector such as those discussed in U.S. patent application Ser. No. 10/746,853, "METHOD AND APPARATUS FOR THIRD HEART SOUND DETECTION," filed on Dec. 24, 2003, now U.S. Pat. No. 7,431,699, assigned to Cardiac Pacemakers, Inc., which is incorporated by reference in its entirety.

Stimulation control circuit 636 is a specific embodiment and includes a synchronization module 638. Synchronization module 638 synchronizes the delivery of the neural stimulation pulses to the predetermined type heart sounds. In one embodiment, stimulation control circuit 636 includes elements corresponding to those of stimulation circuit 336, including offset interval generator 339 and pulse delivery controller 340. Synchronization circuit 638 includes one or both of a continuous synchronization module to synchronize the delivery of the neural stimulation pulses to the predetermined type heart sound of each of consecutive cardiac cycles and a periodic synchronization module to synchronize the delivery of the neural stimulation pulses to the predetermined type heart sound of each of selected cardiac cycles on a periodic basis. The offset interval generator produces an offset interval starting with the detected predetermined type heart sound. The pulse delivery controller sends the pulse delivery signal to start a delivery of a burst of a plurality of neural stimulation pulses when the offset interval expires. In one embodiment, the pulse delivery controller sends the pulse delivery signal after the detection of the predetermined type heart sound for each of consecutive cardiac cycles. In another embodiment, the pulse delivery controller sends the pulse delivery signal after the detection of the predetermined type heart sound for each of selected cardiac cycles according to a predetermined pattern or schedule, such as on a periodic basis.

Figure 7:
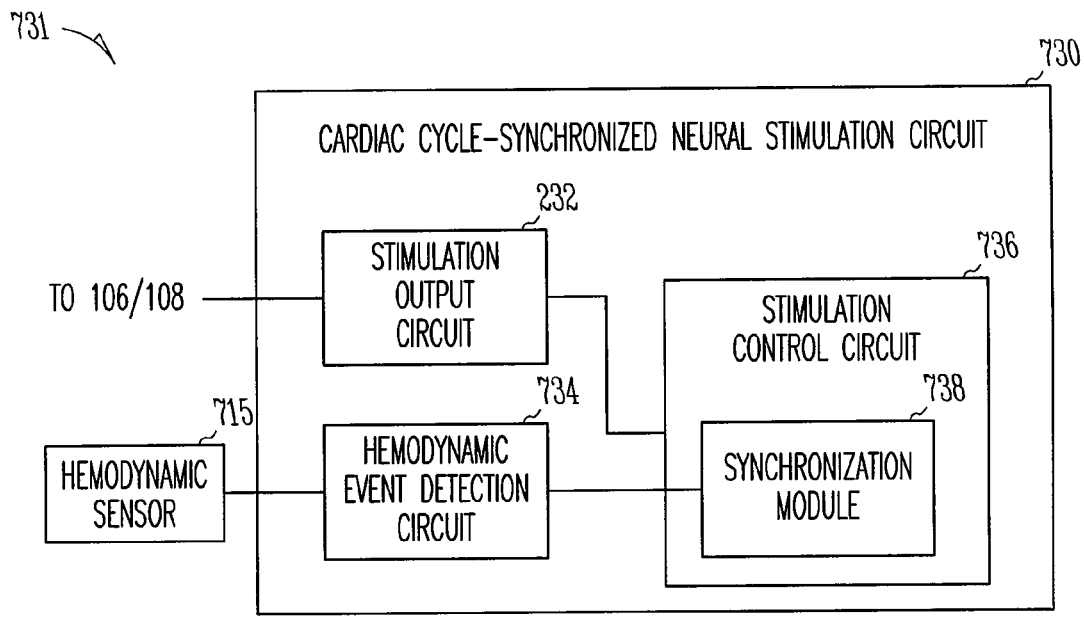
FIG. 7 is a block diagram illustrating an embodiment of a circuit using a hemodynamic signal to synchronize neural stimulation to cardiac cycles.

FIG. 7 is a block diagram illustrating an embodiment of a cardiac cycle-synchronized neural stimulation system 731, which is a specific embodiment of system 231 and uses a hemodynamic signal to synchronize neural stimulation to cardiac cycles. System 731 includes a hemodynamic sensor 715 and a cardiac cycle-synchronized neural stimulation circuit 730, which is a specific embodiment of cardiac cycle-synchronized neural stimulation circuit 230. Cardiac cycle-synchronized neural stimulation circuit 730 includes stimulation output circuit 232, a hemodynamic event detection circuit 734, and a stimulation control circuit 736.

Hemodynamic sensor 715 senses a hemodynamic signal indicative of hemodynamic performance, such as a signal indicative of blood pressure or flow. In one embodiment, hemodynamic sensor 715 is an implantable hemodynamic sensor. In one embodiment, hemodynamic sensor 715 includes a Doppler echocardiographic transducer to sense a peripheral blood flow. In another embodiment, hemodynamic sensor 715 includes a pressure sensor to sense a central or peripheral blood pressure. In another embodiment, hemodynamic sensor 715 includes a pulse oximeter to sense an oximetry signal, which is a plethysmographic signal indicative of blood flow.

Hemodynamic event detection circuit 734 detects predetermined type hemodynamic events from the hemodynamic signal. The hemodynamic events correspond to a recurring feature of the cardiac cycle that is chosen to be a timing reference to which the neural stimulation is synchronized. In one embodiment, hemodynamic event detection circuit 734 includes a peak detector that detects predetermined type peaks in the hemodynamic signal. In one specific embodiment, the peak detector is a pressure peak detector that detects predetermined type peaks in a blood pressure signal. In another specific embodiment, the peak detector includes a flow peak detector that detects predetermined type peaks in a blood flow signal. The predetermined type peaks are peaks indicative of a characteristic event that occurs during each cardiac cycle. In another embodiment, cardiac cycle-synchronized neural stimulation circuit 730 includes a derivative calculator to produce a derivative hemodynamic signal by calculating a time derivative of the hemodynamic signal. Hemodynamic event detection circuit 734 detects the predetermined type hemodynamic event from the derivative hemodynamic signal. In one embodiment, the peak detector detects predetermined type peaks in the derivative hemodynamic signal. In one specific embodiment, the peak detector is a pressure change peak detector that detects predetermined type peaks in a derivative hemodynamic signal indicative of changes in the blood pressure (e.g., dP/dt). In another specific embodiment, the peak detector includes a flow change peak detector that detects predetermined type peaks in a derivative hemodynamic signal indicative changes in the blood flow.

Stimulation control circuit 736 is a specific embodiment and includes a synchronization module 738. Synchronization module 738 synchronizes the delivery of the neural stimulation pulses to the predetermined type hemodynamic events. In one embodiment, stimulation control circuit 736 includes elements corresponding to those of stimulation circuit 336, including offset interval generator 339 and pulse delivery controller 340. Synchronization circuit 738 includes one or both of a continuous synchronization module to synchronize the delivery of the neural stimulation pulses to the predetermined type hemodynamic event of each of consecutive cardiac cycles and a periodic synchronization module to synchronize the delivery of the neural stimulation pulses to the predetermined type hemodynamic event of each of selected cardiac cycles on a periodic basis. The offset interval generator produces an offset interval starting with each detected predetermined type hemodynamic event. The pulse delivery controller sends the pulse delivery signal to start a delivery of a burst of a plurality of neural stimulation pulses when the offset interval expires. In one embodiment, the pulse delivery controller sends the pulse delivery signal after the detection of the predetermined type hemodynamic event for each of consecutive cardiac cycles. In another embodiment, the pulse delivery controller sends the pulse delivery signal after the detection of the predetermined type hemodynamic event for each of selected cardiac cycles according to a predetermined pattern or schedule, such as on a periodic basis.

Figure 8:
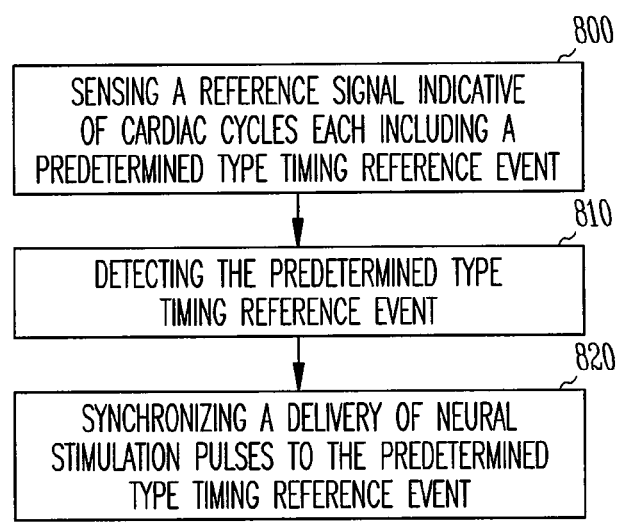
FIG. 8 is a flow chart illustrating an embodiment of a method for synchronizing neural stimulation to cardiac cycles.

FIG. 8 is a flow chart illustrating an embodiment of a method for synchronizing neural stimulation to cardiac cycles. In one embodiment, the method is performed by cardiac cycle-synchronized neural stimulation system 231, including any of its specific embodiments or any combination of its specific embodiments discussed above.

A reference signal is sensed at 800. The reference signal is indicative of cardiac cycles each including a predetermined type timing reference event. In one embodiment, the reference signal is sensed using an implantable sensor placed external to the circulatory system. Examples of the reference signal include a cardiac signal such as a subcutaneous ECG signal, an acoustic signal indicative of heart sounds, and a hemodynamic signal such as a blood pressure or flow signal.

The predetermined type timing reference event is detected at 810. In one embodiment, the reference signal is processed to allow or to facilitate the detection of the predetermined type timing reference event. In one specific embodiment, the predetermined type timing reference event is detected based on the reference signal sensed over a single cardiac cycle. In another embodiment, the predetermined type timing reference event is detected based on the reference signal sensed over a plurality of cardiac cycles. Examples of such processing include filtering, blanking unwanted activities from the reference signal, detecting an intermediate event having an approximately predictable timing relationship with the predetermined type timing reference event, and averaging the reference signal over a plurality of cardiac cycles. Examples of the predetermined type timing reference event include P-wave and R-wave detected from the cardiac signal such as the subcutaneous ECG signal, a predetermined type heart sound from the acoustic signal, and a point of peak amplitude or any other morphologically distinctive point in the hemodynamic signal such as the pressure or flow signal.

A delivery of neural stimulation pulses is synchronized to the predetermined type timing reference event at 820. In one embodiment, the delivery of the neural stimulation pulses is synchronized to the predetermined type timing reference event of each of consecutive cardiac cycles on a continuous basis. In another embodiment, the delivery of the neural stimulation pulses is synchronized to the predetermined type timing reference event of each of selected cardiac cycles on a periodic basis. In one embodiment, a burst of neural stimulation pulses is delivered at the end of an offset interval starting with the predetermined type timing reference event. In one embodiment, the burst of neural stimulation pulses is delivered after the predetermined type timing reference event for each cardiac cycle of consecutive cardiac cycles. In another embodiment, the burst of neural stimulation pulses is delivered after the predetermined type timing reference event for each cardiac cycle of selected cardiac cycles according to a predetermined pattern or schedule, such as on a period basis.

In one embodiment, the delivery of the neural stimulation pulses is further controlled by the patient's cardiac condition and/or activity level. The patient's cardiac rhythm and one or more cardiac parameters indicative of the cardiac functions are monitored. In one embodiment, the delivery of the neural stimulation pulses is controlled based on the cardiac rhythm. In response to a detected arrhythmia, the delivery of the neural stimulation pulses is withheld or adjusted. In another embodiment, the delivery of the neural stimulation pulses is adjusted or optimized based on the one or more cardiac parameters. Examples of such cardiac parameters include heart rate, atrioventricular intervals, and interventricular intervals. The timing for the delivery of the neural stimulation pulses is adjusted, for example, for a desirable heart rate, an atrioventricular interval corresponding to a desirable hemodynamic performance, and/or a minimum interventricular interval.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of legal equivalents to which such claims are entitled.

What is claimed is:

1. A method for operating a neural stimulation system coupled to a living subject having a circulatory system, the method comprising:

delivering neural stimulation pulses from an implantable medical device;

sensing a reference signal indicative of cardiac cycles each including a predetermined type timing reference event using an implantable reference signal sensor placed external to the circulatory system, wherein sensing the reference signal includes sensing a subcutaneous ECG signal using implantable electrodes incorporated onto the implantable medical device;

detecting the predetermined type timing reference event from the reference signal;

measuring an atrioventricular interval using the subcutaneous ECG signal; and controlling the delivery of the neural stimulation pulses using the detected predetermined type timing reference event and the measured atrioventricular interval, including synchronizing the delivery of the neural stimulation pulses to the detected predetermined type timing reference event.

2. The method of claim 1, wherein detecting the predetermined type timing reference event from the reference signal comprises detecting an atrial depolarization (P-wave) from the subcutaneous ECG signal.

3. The method of claim 1, further comprising staring an offset interval with the detected timing reference event, and wherein synchronizing the delivery of the neural stimulation pulses to the detected timing reference event comprises starting a delivery of a burst of a plurality of neural stimulation pulses when the offset interval expires.

4. The method of claim 3, wherein synchronizing the delivery of the neural stimulation pulses comprises synchronizing the delivery of the neural stimulation pulses to the timing reference event of consecutive heart beats on a continuous basis.

5. The method of claim 3, wherein synchronizing the delivery of the neural stimulation pulses comprises synchronizing the delivery of the neural stimulation pulses to the timing reference event of selected heart beats on a periodic basis.

6. The method of claim 3, wherein detecting the timing reference event from the reference signal comprises extracting the timing reference event from a segment of the reference signal recorded during a plurality of cardiac cycles.

7. The method of claim 1, further comprising:
detecting an arrhythmia from the subcutaneous ECG signal; and
adjusting the delivery of the neural stimulation pulses in response to the arrhythmia being detected.

8. The method of claim 2, wherein detecting the P-wave comprises:
averaging the subcutaneous ECG signal over a plurality of cardiac cycles; and
detecting the P-wave using the averaged subcutaneous ECG signal.

9. The method of claim 2, wherein detecting the P-wave comprises:
detecting a ventricular depolarization (R-wave) from the subcutaneous ECG signal; and
generating a timing interval upon detection of the R-wave, such that the P-wave is estimated to occur at an end of the timing interval.

10. The method of claim 1, wherein synchronizing the delivery of the neural stimulation pulses to the detected predetermined type timing reference event comprises:
producing an offset interval starting with the predetermined type timing reference event; and
delivering a burst of the neural stimulation pulses upon expiration of the offset interval.

11. The method of claim 1, wherein detecting the predetermined type timing reference event comprises detecting the predetermined type timing reference event from the subcutaneous ECG signal for each of the cardiac cycles, and synchronizing the delivery of the neural stimulation pulses to the detected predetermined type timing reference event comprises synchronizing the delivery of the neural stimulation pulses to the predetermined type timing reference event consecutively for the each of the cardiac cycles.

12. The method of claim 1, wherein sensing the subcutaneous ECG signal comprises sensing the subcutaneous ECG signal using one or more electrodes incorporated onto a header of the implantable medical device, the header attached to a can of the implantable medical device and including connectors configured to provide for electrical access to a circuit housed in the can.

13. The method of claim 12, wherein sensing the subcutaneous ECG signal comprises sensing the subcutaneous ECG signal using one or more electrodes incorporated onto the can.

14. The method of claim 13, wherein sensing the subcutaneous ECG signal comprises sensing the subcutaneous ECG signal using a plurality of concentric electrodes.

15. The method of claim 14, wherein sensing the subcutaneous ECG signal comprises sensing the subcutaneous ECG signal using an electrode having a shape approaching a contour of the can.

16. The method of claim 1, wherein detecting the predetermined type timing reference event from the reference signal comprises detecting a ventricular depolarization (R-wave) from the subcutaneous ECG signal.

17. The method of claim 1, wherein synchronizing the delivery of the neural stimulation pulses to the detected predetermined type timing reference event comprises synchronizing the delivery of the neural stimulation pulses for each selected cardiac cycle of the cardiac cycles according to a predetermined pattern or schedule.

18. The method of claim 17, wherein synchronizing the delivery of the neural stimulation pulses to the detected predetermined type timing reference event comprises synchronizing the delivery of the neural stimulation pulses periodically.

19. The method of claim 1, further comprising detecting an arrhythmia from the subcutaneous ECG signal, withholding or adjusting the delivery of the neural stimulation pulses when the arrhythmia is detected.

20. The method of claim 1, further comprising measuring a heart rate, and wherein controlling the delivery of the neural stimulation pulses comprises controlling the delivery of the neural stimulation pulses using the detected predetermined type timing reference event, the measured atrioventricular interval, and the heart rate.

* * * * *